United States Patent [19]

Itoh et al.

[11] Patent Number: 5,360,783

[45] Date of Patent: Nov. 1, 1994

[54] WATER-BASED PESTICIDAL COMPOSITION

[75] Inventors: Shinichi Itoh; Kenji Kuno; Akio Hoshino, all of Aichi, Japan

[73] Assignee: Takemoto Yushi Kabushiki Kaisha, Aichi, Japan

[21] Appl. No.: 39,519

[22] Filed: Mar. 29, 1993

Related U.S. Application Data

[63] Continuation-in-part of Ser. No. 902,461, Jun. 19, 1992, abandoned, which is a continuation of Ser. No. 557,902, Jul. 25, 1990, abandoned.

[30] Foreign Application Priority Data

Jul. 26, 1989 [JP] Japan .................. 1-193577

[51] Int. Cl.$^5$ ............................. A01N 25/30
[52] U.S. Cl. ..................... 504/305; 504/116; 514/120; 514/487; 514/490; 514/492; 514/646; 514/788; 71/DIG. 1
[58] Field of Search ............... 504/116, 305; 71/DIG. 1; 514/120, 487, 490, 492, 646, 788

[56] References Cited

U.S. PATENT DOCUMENTS

| | | | |
|---|---|---|---|
| 4,303,640 | 12/1981 | Fuyama et al. | 424/78 |
| 4,606,913 | 8/1986 | Aronson et al. | 424/59 |
| 4,770,803 | 9/1988 | Forsberg | 252/75 |

*Primary Examiner*—Richard L. Raymond
*Assistant Examiner*—S. Mark Clardy
*Attorney, Agent, or Firm*—Heller, Ehrman, White & McAuliffe

[57] ABSTRACT

A water-based pesticidal composition contains 100 weight parts of substantially water-insoluble pesticide and 1.7–200 weight parts of a surface active agent. The surface active agent contains Component A and Component B at weight ratio of A/B=80/20–20/80. Component A is polyalkylene glycol ether derivative of polyethylene polyamine shown by the following general formula and having molecular weight of 20,000–100,000:

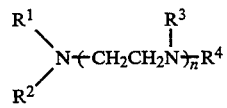

where $R^1$, $R^2$, $R^3$ and $R^4$ are selected from the group consisting of hydrogen, alkyl group with 1–4 carbon atoms, alkanoyl group with 2–18 carbon atoms, alkenoyl group with 2–18 carbon atoms and polyoxyalkylene glycol group containing oxyethyne unit and oxypropylene unit at weight ratio of (oxyethyne unit/oxypropylene unit=)100/0–50/50, at least one of $R^1$, $R^2$, $R^3$ and $R^4$ being the polyoxyalkylene glycol group, and n is an integer 2–250. Component B includes one or more selected from the group consisting of partial esters of polyhydric alcohol selected from sorbitol, sorbitan, glycerine and polyglycerine and unsaturated aliphatic acid with 16–22 carbon atoms and ethylene oxide adducts of such partial esters.

8 Claims, No Drawings

WATER-BASED PESTICIDAL COMPOSITION

This is a continuation-in-part of patent application Ser. No. 07/902,461 filed Jun. 19, 1992, now abandoned, which is a continuation of patent application Ser. No. 07/557,902 filed Jul. 25, 1990, now abandoned.

BACKGROUND OF THE INVENTION

This invention relates to a pesticidal composition having a pesticide suspended or emulsified in a water-based medium.

Pesticides such as insecticides, fungicides and herbicides are generally prepared into an appropriate formulation such as an emulsifiable concentrate, wettable powder, dust or granules, depending upon their individual characteristics and purpose of use, before they are put to a practical use. Recently, water-based suspension concentrates (hereinafter abbreviated into SC) having a pesticide suspended in a water-based medium and water-based concentrated emulsions (hereinafter abbreviated into EW) having a pesticide in the form of an emulsion are coming to be favorably considered from the point of view of human safety and environmental protection from these pesticidal formulations. These SCs and EWs, however, are required to be stable such that there is no sedimentation, flocculation or gelation of their suspended or emulsified particles.

Examples of dispersant conventionally used for the preparation of SCs and EWs include non-ionic surfactants such as polyoxyethylated alkylphenol, polyoxyethylated polyarylphenol, sorbitan fatty acid esters and polyoxyethylated sorbitan fatty acid esters, and anionic surfactants such as many kinds of sulfonates, sulfates and phosphates. Examples of known stabilizer for dispersion of an emulsion (protective colloid) to be used with such a dispersant include synthetic organic high molecular compounds such as carboxymethyl cellulose, polyethylene oxides and polyvinyl alcohols and natural sugar derivatives such as xanthan gum, guar gum and sodium alginate. Japanese Patent Publications Tokko 58-24401, Tokkai 61-126001 and Tokkai 63-8301 and European Patent EP-261492, for example, disclose examples of SC as water-based pesticidal formulations using these known dispersants and stabilizers. U.S. Pat. No. 4,303,640, Japanese Patent Publications Tokko 63-32046, Tokkai 58-131902 and Tokkai 63-198605 and British Patent 2,048,675, for example, disclose examples of EW as water-based pesticidal formulations using these known dispersants and stabilizers.

With these prior art SC and EW using known dispersants and stabilizers, however, there remain the problems of sedimentation, flocculation and gelation of the suspended or emulsified particles, thereby adversely affecting not only the stability of the water-based pesticidal formulations but also their handling and biological activities. In particular, the stability of a water-based pesticidal formulation decreases as its pesticide concentration increases. The viscosity of the system increases significantly in such a case and this introduces additional limitations in the selection of apparatus for its preparation as well as its load.

SUMMARY OF THE INVENTION

It is therefore an object of the present invention to provide new water-based pesticidal compositions with which the problems associated with prior art compositions can be solved.

The present invention has been achieved by the present inventors as a result of their diligent studies in view of the above and other objects and is based on their discovery that a desired result can be obtained if use as a dispersant for emulsion is made of specified amounts respectively of polyalkylene glycol ether derivative of polyethylene polyamine having a specified structure and unsaturated aliphatic partial ester of polyhydric alcohol or its ethylene oxide adduct.

DETAILED DESCRIPTION OF THE INVENTION

This invention relates to a pesticidal composition having a pesticide suspended or emulsified in a water-based medium, comprising 100 weight parts of substantially water-insoluble pesticide and 1.7-200 weight parts of a surface active agent containing Component A and Component B at weight ratio of A/B=80/20-20/80 where Component A is polyalkylene glycol ether derivative of polyethylene polyamine shown by the following general formula and having molecular weight of 20,000-100,000:

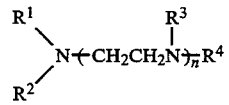

where $R^1$, $R^2$, $R^3$ and $R^4$ are selected from the group consisting of hydrogen, alkyl group with 1-4 carbon atoms, alkanoyl group with 2-18 carbon atoms, alkenoyl group with 2-18 carbon atoms and polyoxyalkylene glycol group containing oxyethyne unit and oxypropylene unit at weight ratio of (oxyethyne unit/oxypropylene unit=)100/0-50/50, at least one of $R^1$, $R^2$, $R^3$ and $R^4$ being such polyoxyalkylene glycol group, and n is an integer 2-250, and Component B includes one or more selected from the group consisting of partial esters of polyhydric alcohol selected from sorbitol, sorbitan, glycerine and polyglycerine and unsaturated aliphatic acid with 16-22 carbon atoms and ethylene oxide adducts of such partial esters.

The pesticides according to the present invention are those with extremely small water solubility or no water solubility at all, regardless of whether they are liquid or solid at room temperature, that is, they are substantially insoluble to water. Examples of such pesticide include o,o-dimethyl-o-4-methylthio-m-tolyl phosphorothioate (Baycid), s-4-chlorobenzyldiethylthio carbamate (Saturn), s-α-ethoxycarbonyl benzyl-o,o-dimethyl phosphorodithioate (Elsan), o-sec-butylphenyl methylcarbamate (BPMC), 2,4,5,6-tetrachloro-1,3-isophthalonitrile (Daconil), dimethyl-4,4-(o-phenylene)bis(3-thioallophanate) (Topsin-Methyl), 4,5,6,7-tetrachlorophthalide (Rabcide), o,o-diethyl-o-(2,3-dihydro-3-oxo-2-phenyl pyridazin-6-yl) phosphorothioate (Ofunack) and manganese ethylene bis (dithiocarbamate) (Maneb).

Component A which is used as a component of surface active agent according to the present invention is a polyalkylene glycol ether derivative of polyethylene polyamine having a specified structure as shown above. Such a derivative can be obtained by using as starting material polyethylene polyamine having three or more amino groups in its molecule or its partially alkylated or acylated derivative and by a reaction between the active hydrogen groups connected to these amino groups and alkylene oxide having ethylene oxide as its indispensable component. Examples of polyethylene polyamine to be thus used include diethylene triamine, triethylene tetramine, tetraethylene pentamine, pentaethylene hexamine and ring-opening polymers of ethylene imine known as polyethylene imines with average molecular weight of 300–10000. Examples of partially alkylated or acylated polyethylene polyamine obtained by partially alkylating or acylating the amino groups of such polyethylene polyamine include N-methyl polyethylene polyamine, N-butyl polyethylene polyamine, N-octyl polyethylene polyamine, N-octadecenyl polyethylene polyamine, N-acetyl polyethylene polyamine, N-butanoyl polyethylene polyamine, N-octanoyl polyethylene polyamine, N-oleoyl polyethylene polyamine and N-octadecanoyl polyethylene polyamine. The alkylene oxide to be used for obtaining polyalkylene glycol derivative from such polyalkylene polyamines or their partially alkylated or acylated derivatives must necessarily include ethylene oxide but may also include, for example, propylene oxide. Practical examples of such polyalkylene glycol derivative include polyethylene glycol ether derivatives with ethylene oxide added singly as well as polyalkylene glycol ether derivatives with mixed block or random additions of both ethylene oxide and propylene oxide. If a mixture of both ethylene oxide and propylene oxide is added, the mixing ratio of ethylene oxide should be 50 weight % or greater. If this ratio is less than 50 weight %, the resultant polyalkylene glycol derivative has reduced water solubility.

The molecular weight of the polyethylene polyamine to be used as the material for Component A of the present invention should preferably be 300 or greater according to the purpose for which it is used. This corresponds to n being 7 or greater in the chemical formula. Similarly, the molecular weight of Component A should be preferably 20,000–100,000 and more preferably 50,000–90,000.

The water-based pesticidal compositions of the present invention are characterized wherein Component A and Component B are both used as a surface active agent. Component B is partial ester of polyhydric alcohol and unsaturated aliphatic acid obtained by an esterification reaction of polyhydric alcohol and unsaturated aliphatic acid or by inter-molecular or intra-molecular dehydrating condensation of this polyhydric alcohol which accompanies the reaction, or ethylene oxide adduct of such partial ester. Examples of this polyhydric alcohol include sorbitol, sorbitan, glycerine and polyglycerine. Examples of this unsaturated aliphatic acid include monoethylenic acid, dienoic and trienoic acid with 16–22 carbon atoms either as a simple substance or a mixture. Particularly preferable, however, are those rich in glycerides, for example, of palmitoleic acid, oleic acid, linoleic acid and ricinoleic acid and obtainable from animal or vegetable oil. Examples of Component B obtainable from such polyhydric alcohol and such unsaturated aliphatic acid include sorbitan monooleate, sorbitan trioleate, glycerine monooleate, glycerine sesqui mono-di ester of soybean fatty acid and aliphatic acid, glycerine monoeruciate, diglycerine dioleate and triglycerine trioleate. Ethylene oxide adducts of such a partial ester can be obtained by adding ethylene oxide to free hydroxyl groups in the partial ester. It is preferable that 20 mols or less of ethylene oxide be added to one mol of the partial ester.

According to the present invention, the ratio between Component A and Component B (A/B) should be 80/20–20/80 by weight. Depending on the purpose of use, however, a ratio in the range of 65/35–35/65 is particularly preferable.

To summarize, water-based pesticidal compositions of the present invention are characterized as containing a pesticide and a surface active agent having Component A and Component B as its indispensable constituents. The pesticide content in the composition is in the range of 10–60 weight %, preferably in the range of 20–60 weight %. If the weight percentage exceeds this range, sedimentation, flocculation and gelation of the suspended or emulsified particles tend to occur easily, adversely affecting the stability. If the weight percentage does not reach this range, it may become necessary to use an increased amount of the composition for obtaining the same result. The amount of surface active agent to be used is about 1.7–200 weight parts for 100 weight parts of the pesticide but a ratio of 3–100 weight parts to 100 weight parts of the pesticide is particularly desirable, depending on the purpose of use.

The water-based pesticidal compositions of the present invention can be produced by known methods. If the pesticide to be used is a solid under the temperature condition, a SC may be obtained by a wet grinding equipment such as a sand grinder or a sand mill using inorganic media. If the pesticide is in the form of a paste or a liquid under the temperature condition of its production, on the other hand, an EW may be obtained by means of an emulsifying apparatus such as a homomixer or a homogenizer. The particle size of emulsified or suspended substances in the water-based pesticidal compositions thus produced may be kept up to be less than 5 $\mu$m in diameter even after 60 days of storage at temperatures of $-5°\sim50°$ C.

The description given above of the present invention is not intended to limit the scope of the invention. The water-based pesticidal compositions of the present invention many include additional components besides the surface active agent described above, depending on the purpose of use and within the limitation that the principal objects of the present invention are not adversely affected. Such additional component includes thickeners, anti-freezing agents, anti-forming agents, antiseptics and pH buffers.

In what follows, the invention is explained by way of practical examples but it goes without saying that these examples are intended to be merely illustrative and not limitative.

TEST 1

A test example of Component A (to be identified as A-1), which is one of the constituents of the surface active agent for the present invention, was prepared as described below. Other test examples of Component A (A-2 through A-5) shown in Table 1, as well as comparison examples shown in Table 2 were also synthesized.

(Synthesis of A-1)

After 360 g of polyethylene imine (average molecular weight=1200) was placed inside an autoclave and the interior of the reaction system was replaced by nitrogen gas, 600 g of propylene oxide was introduced with pressure into the autoclave over a period of 3 hours at 80° C. in the absence of any catalyst. After a reaction was continued for 30 minutes at 80°–100° C., 83 g of potassium hydoxide was added and a mixture of 1850 g of propylene oxide and 22100 g of ethylene oxide was introduced with pressure into the autoclave over a period of about 24 hours at 120°–150° C. After a reaction was continued for 2 hours at the same temperature, 24900 g of a dispersant (A-1) was obtained. The hydroxyl value of A-1 was 20.5 and its average molecular weight calculated from this hydroxyl value was 83400. In Tables 1 and 2, AO indicates alkylene oxide, EO indicates ethylene oxide and PEPA indicates polyethylene imine.

TABLE 1

| Component A | Starting Material Kind | Average Molecular Weight | Average Molecular Weight | AO Addition | EO Weight % |
|---|---|---|---|---|---|
| A-1 | PEPA | 1200 | 83400 | Block/Random | 90 |
| A-2 | PEPA | 600 | 72100 | Block | 80 |
| A-3 | PEPA | 300 | 81300 | Block | 90 |
| A-4 | PEPA | 600 | 24400 | Block | 90 |
| A-5 | PEPA | 1200 | 52500 | — | 100 |

TABLE 2

| Surface Active Agent | Starting Material Kind | Average Molecular Weight | Average Molecular Weight | AO Additon | EO Weight % |
|---|---|---|---|---|---|
| R-1 | Ethylene diamine | — | 15000 | Block | 90 |
| R-2 | Ethylene diamine | — | 8300 | Block | 90 |
| R-3 | PEPA | 600 | 12200 | Block | 40 |
| R-4 | PEPA | 1200 | 81300 | Block | 30 |

TEST 2

Mixed together were 41 weight parts of Maneb (solid) as pesticide, 5 weight parts of propylene glycol as anti-freezing agent, 4 weight parts of a surface active agent and 50 weight parts of water. After glass beads of 2 mm$\phi$ (100 weight parts) were added to this mixture and subjected to a wet grinding process, the beads were removed and a Maneb SC was prepared. For each Maneb SC agent thus obtained, its appearance was evaluated and its suspension or emulsion stability and particle size ($\mu$) were measured as explained below. The results are shown in Table 3 (for test examples) and Table 4 (for comparison examples).

Evaluation of Appearance Immediately Afterward

The appearance of each Maneb SC was observed immediately after it was prepared and was evaluated as follows:
A: Good suspended or emulsified condition;
B: Fairly good suspended or emulsified condition;
C: Unsatisfactory suspended or emulsified condition.

Evaluation of Appearance After Storage

Immediately after each Maneb SC agent was prepared, 50 g thereof was placed inside a glass container of diameter 38 mm and capacity 100 ml, the container was sealed and stored for 60 days during which temperature was kept at −5° C. for three days and 50° C. for three days, this cycle being repeated 10 times. Thereafter, each sample was evaluated as follows:
A: Good suspended or emulsified condition as immediately after the preparation;
B: Sedimentation of particles is slightly noticeable but easily re-emulsified or re-dispersed by shaking or mixing;
C: Particle sedimentation and separation are noticeable and difference is significant from the condition immediately after the preparation;
D: Significant particle sedimentation and separation.

Measurement of Stability

Use was made of both the samples observed immediately after the preparation and those stored for 60 days as described above to measure for each the ratio of the height of the suspended or emulsified part to the total liquid height.

Measurement of Particle Size

Use was made of both the Maneb SC observed immediately after the preparation and those stored for 60 days as described above and the average diameter ($\mu$) of suspended or emulsified particles was measured in each by using centrifuged sedimentation particle size analyzer CAPA700 (trade name of and produced by Horiba and Co. Ltd.). The results are shown in Tables 3 and 4, where
B-1: Sorbitan monooleate;
B-3: Glycerine monooleate;
-: No measurement taken because it was inappropriate as water-based pesticide for lack of flowability or presence of oil separation, or because it was solidified and did not re-emulsify or re-disperse;
R-5: Polyoxyethylene polyoxypropylene block polyether (average molecular weight=20000, ethylene oxide=70 weight %);
R-6: Phosphate ester sodium salt of R-5;
R-7: Polyvinyl alcohol (saponification=88%, degree of polymerization=1700);
R-8: Polyoxyethylene (30 mol) tristyryl phenylether.

TABLE 3

| | Surface Active Agent | | Appearance | | Stability | Particle Diameter ($\mu$) | |
|---|---|---|---|---|---|---|---|
| No. | Component | Part | Immediately After | After Storage | % | Immediately After | After Storage |
| 1 | A-2 | 6 | A | A | 95 | 1.8 | 1.8 |
|   | B-1 | 4 |   |   |   |   |   |
| 2 | A-2 | 6 | A | A | 96 | 1.7 | 1.8 |
|   | B-3 | 4 |   |   |   |   |   |

TABLE 4

(Comparison Examples)

| No. | Surface Active Agent Component | Appearance Immediately After | Appearance After Storage | Stability % | Particle Diameter (μ) Immediately After | Particle Diameter (μ) After Storage |
|---|---|---|---|---|---|---|
| 1 | R-1 | B | D | 80 | — | — |
| 2 | R-2 | B | C | 83 | — | — |
| 3 | R-3 | B | C | 90 | — | — |
| 4 | R-4 | B | D | 95 | — | — |
| 5 | R-5 | B | D | — | — | — |
| 6 | R-6 | B | D | — | — | — |
| 7 | R-7 | B | D | — | — | — |
| 8 | R-8 | B | D | — | — | — |

TEST 3

Use was made of 50 weight parts of Elsan (liquid) as pesticide, 5 weight parts of propylene glycol as anti-freezing agent, 9 weight parts of surface active agent (except 10 weight parts for Comparison Example 10 and 8 weight parts for Comparison Example 11) and 36 weight parts of water (except 35 weight parts for Comparison Example 10 and 37 weight parts for Comparison Example 11), mixed together to prepare Elsan EW by using a homomixer to mix and stir for 5 minutes at 7000 rpm. Each Elsan EW was tested as in Test 2. The results are shown in Tables 5 and 6, where:

B-2: Sorbitan trioleate;
B-4: Glycerine trioleate;
B-5: Polyoxyethylene (20 mol) sorbitan monooleate;
B-6: Polyoxyethylene (20 mol) sorbitan trioleate.

TEST 4

Each of the EW shown in Tables 7 and 8 was prepared similarly as in Test 3. These EW are characterized as each containing 5 weight parts of propylene glycol as anti-freezing agent and water to make a total of 100 weight parts. Each of these EW was tested as in Test 2, the results being shown in Tables 7 and 8, where:

R-9: Carboxy methyl cellulose;
R-10: Xanthum gum;
R-11: Dodecyl benzene sulfonate Ca salt;
R-12: Sulfonated polyvinyl alcohol (average molecular weight=3000).

TEST 5

Each of the SC shown in Tables 9 and 10 was prepared similarly as in Test 2. These SC are characterized as each containing 5 weight parts of propylene glycol as

TABLE 5

(Test Examples)

| No. | Surface Active Agent Component | Part | Appearance Immediately After | Appearance After Storage | Stability % | Particle Diameter (μ) Immediately After | Particle Diameter (μ) After Storage |
|---|---|---|---|---|---|---|---|
| 3 | A-1 | 4 | A | A | 98 | 1.2 | 1.3 |
|   | B-1 | 5 |   |   |   |   |   |
| 4 | A-5 | 4 | A | A | 93 | 1.5 | 1.8 |
|   | B-2 | 5 |   |   |   |   |   |
| 5 | A-2 | 4 | A | A | 97 | 1.4 | 1.6 |
|   | B-3 | 5 |   |   |   |   |   |
| 6 | A-3 | 4 | A | A | 92 | 1.4 | 1.6 |
|   | B-4 | 5 |   |   |   |   |   |
| 7 | A-4 | 4 | A | A | 92 | 1.2 | 1.6 |
|   | B-5 | 5 |   |   |   |   |   |
| 8 | A-4 | 4 | A | B | 85 | 1.2 | 1.7 |
|   | B-6 | 5 |   |   |   |   |   |

TABLE 6

(Comparison Examples)

| No. | Surface Active Agent Component | Part | Appearance Immediately After | Appearance After Storage | Stability % | Particle Diameter (μ) Immediately After | Particle Diameter (μ) After Storage |
|---|---|---|---|---|---|---|---|
| 9 | R-1 | 4 | B | D | 50 | 3.0 | 8.0 |
|   | B-1 | 5 |   |   |   |   |   |
| 10 | R-2 | 5 | A | D | — | — | — |
|   | B-5 | 5 |   |   |   |   |   |
| 11 | R-3 | 3 | B | D | 61 | 4.0 | 9.0 |
|   | B-3 |   |   |   |   |   |   |
| 12 | R-4 | 4 | B | D | 50 | 1.5 | 5.0 |
|   | B-4 | 5 |   |   |   |   |   |
| 13 | R-5 | 4 | B | D | 63 | 1.5 | 7.0 |
|   | B-1 | 5 |   |   |   |   |   |
| 14 | R-6 | 4 | B | D | — | — | — |
|   | B-1 | 5 |   |   |   |   |   | anti-freezing agent and water to make a total of 100 weight parts. Each of these SC was tested as in Test 2, the results being shown in Tables 9 and 10, where:
R-13: Carboxy methyl cellulose;
R-14: Polyoxyethylene (10 mol) nonylphenyl ether;
R-15: Alkyl naphthalene sulfonate Na salt;
R-16: Dioctyl sulfosuccinate Na salt;
R-17: Guar gum;
R-18: Sucrose monolaurate.

These tables show clearly that the water-based pesticidal compositions embodying the present invention are extremely stable.

TABLE 7
(Test Examples)

| No. | Pesticide Type | Part | Surface Active Agent Comp't | Part | Appearance Immed'ly After | After Storage | Stability % | Particle Size (μ) Immed'ly After | After Storage |
|---|---|---|---|---|---|---|---|---|---|
| 9 | Saturn | 55 | A-1<br>B-1 | 4<br>3 | A | A | 98 | 0.9 | 1.1 |
| 10 | Saturn | 55 | A-1<br>B-5 | 4<br>3 | A | A | 96 | 1.0 | 1.5 |
| 11 | BPMC | 25 | A-2<br>B-5 | 4<br>5 | A | A | 98 | 0.8 | 1.2 |

TABLE 8
(Comparison Examples)

| No. | Pesticide Type | Part | Surface Active Agent Comp't | Part | Appearance Immed'ly After | After Storage | Stability % | Particle Size (μ) Immed'ly After | After Storage |
|---|---|---|---|---|---|---|---|---|---|
| 15 | Saturn | 55 | A-1<br>B-1 | 0.3<br>0.3 | C | D | — | — | — |
| 16 | Saturn | 55 | R-1<br>B-1 | 4<br>3 | A | D | — | — | — |
| 17 | Saturn | 55 | R-3<br>B-1 | 4<br>3 | B | D | — | — | — |
| 18 | Saturn | 55 | R-4<br>B-1 | 4<br>3 | C | D | — | — | — |
| 19 | BPMC | 25 | R-8 | 5 | A | D | — | — | — |
| 19-1 | Saturn | 55 | R-7<br>R-9 | 5<br>2 | B | C | 43 | 2.1 | 2.7 |
| 19-2 | BPMC | 25 | R-10<br>R-11 | 1<br>4 | A | C | 42 | 1.8 | 2.6 |
| 19-3 | BPMC | 25 | R-12 | 5 | B | C | 45 | 2.2 | 2.7 |

TABLE 9
(Test Examples)

| No. | Pesticide Type | Part | Surface Active Agent Comp't | Part | Appearance Immed'ly After | After Storage | Stability % | Particle Size (μ) Immed'ly After | After Storage |
|---|---|---|---|---|---|---|---|---|---|
| 12 | Ofunack | 26 | A-5<br>B-1 | 5<br>5 | A | A | 91 | 1.2 | 1.4 |
| 13 | Daconil | 42 | A-1<br>B-5 | 4<br>5 | A | A | 89 | 2.3 | 2.4 |
| 14 | Topsin-M | 46 | A-2<br>B-1 | 4<br>2 | A | A | 87 | 3.2 | 3.3 |

TABLE 10
(Comparison Examples)

| No. | Pesticide Type | Part | Surface Active Agent Comp't | Part | Appearance Immed'ly After | After Storage | Stability % | Particle Size (μ) Immed'ly After | After Storage |
|---|---|---|---|---|---|---|---|---|---|
| 20 | Ofunack | 26 | R-4 | 5 | B | C | 52 | 3.5 | 7.2 |
| 21 | Ofunack | 26 | A-5<br>B-1 | 0.3<br>0.3 | C | D | — | — | — |
| 22 | Ofunack | 26 | R-6 | 5 | A | D | — | — | — |
| 23 | Ofunack | 26 | R-7 | 4 | A | D | — | — | — |
| 24 | Daconil | 42 | R-1 | 2 | A | C | 53 | 2.4 | 2.6 |
| 25 | Daconil | 42 | R-5 | 3 | A | C | 52 | 2.3 | 2.5 |
| 26 | Topsin-M | 46 | R-3<br>B-1 | 4<br>2 | A | C | 56 | 3.0 | 3.2 |
| 27 | Topsin-M | 46 | R-3 | 6 | A | C | 52 | 2.9 | 3.3 |

What is claimed is:

1. A water-based pesticidal composition containing 10~60 weight % of a pesticide with average particle size less than 5 μm in diameter suspended or emulsified in a water-based medium, said composition comprising
   100 weight parts of substantially water-insoluble pesticide selected from the group consisting of insecticides, fungicides and herbicides, and
   1.7-200 weight parts of a surface active agent containing Component A and Component B at weight ratio of A/B=80/20-20/80,
   where Component A is polyalkylene glycol ether derivative of polyethylene polyamine shown by the following general formula and having molecular weight of 20,000-100,000:

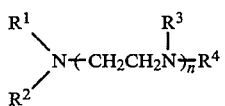

where $R^1$, $R^2$, $R^3$ and $R^4$ are selected from the group consisting of hydrogen and polyoxyalkylene glycol group containing oxyethyne unit and oxypropylene unit at weight ratio of (oxyethyne unit/oxypropylene unit=)100/0-50/50, at least one of $R^1$, $R^2$, $R^3$ and $R^4$ being said polyoxyalkylene glycol group, and n is an integer 2-250, and
   where Component B includes one or more selected from the group consisting of partial esters of polyhydric alcohol selected from sorbitol and sorbitan, and unsaturated aliphatic acid with 16-22 carbon atoms and ethylene oxide adducts of said partial esters.

2. The water-based pesticidal composition of claim 1 wherein said Components A and B are contained at weight ratio of A/B=65/35-35/65.

3. The water-based pesticidal composition of claim 1 where said pesticide and said surface active agent are contained at relative weight ratio of 100/3-100/100.

4. The water-based pesticidal composition of claim 2 where said pesticide and said surface active agent are contained at relative weight ratio of 100/3-100/100.

5. The water-based pesticidal composition of claim 1 which is a concentrated emulsion.

6. The water-based pesticidal composition of claim 2 which is a concentrated emulsion.

7. The water-based pesticidal composition of claim 3 which is a concentrated emulsion.

8. The water-based pesticidal composition of claim 4 which is a concentrated emulsion.

* * * * *